United States Patent [19]

Weissman et al.

[11] Patent Number: 4,835,255

[45] Date of Patent: May 30, 1989

[54] T-CELL MEMBRANE PROTEIN

[75] Inventors: Sherman M. Weissman, New Haven, Conn.; Miguel A. Alonso, Madrid, Spain

[73] Assignee: Yale University, New Haven, Conn.

[21] Appl. No.: 31,316

[22] Filed: Mar. 26, 1987

[51] Int. Cl.[4] .................. C07K 13/00; C07K 7/08; C07K 7/06

[52] U.S. Cl. ................... 530/350; 530/327; 530/326

[58] Field of Search .............. 530/326, 327, 350

[56] References Cited

FOREIGN PATENT DOCUMENTS 0149548 7/1985 European Pat. Off. .
0200350 11/1986 European Pat. Off. .

OTHER PUBLICATIONS

Proc. Nat'l. Acad. Sci. 83 (1986), 742–746.
The Journal of Immunology 137, 2043–2049 (1986).
Brenner et al., (1987) Chemical Abstracts 106, Abstract No. 136555z.
Alonso et al., (1988) Chemical Abstracts 108, Abstract No. 107319m.
Krangel et al., (1987) Science 237:64–67.
Sutcliffe, J. G., et al., Antibodies that React with Predetermined Sites on Proteins, Science, 219:660.
Berzofsky, J. A., Intrinsic and Extrinsic Factors in Protein Antigenic Structure, Science, 229:932.
The Merck Manual of Diagnosis and Therapy, Fifteenth Edition, 1987, 1176–1181.
Alonso, M. A., et al., cDNA Cloning and Sequence of MAL, a Hydrophobic Protein Associated with Human T-Cell Differentiation, Proc. Natl, Acad. Sci., USA, 84:1997–2001.
Hedrick et al., (1984) Nature 308:149–153.

*Primary Examiner*—Delbert R. Phillips
*Attorney, Agent, or Firm*—Peter J. Dehlinger

[57] ABSTRACT

A 16.7 kilodalton membrane protein which is produced in mature, but no early-stage, T cells has been discovered. The protein has four distinct amphipathic domains, each having an amino acid composition which is predictive of an alpha helical structure that would be stable in a lipid bilayer. Each of these regions is flanked by a relatively polar domain whose amino acid sequence is predictive of $\beta$ pleat peptide regions. An antibody specific against one of the polar domains can be used to discriminate mature T-cells in a mixed-cell sample.

3 Claims, 5 Drawing Sheets

FIG. 1A
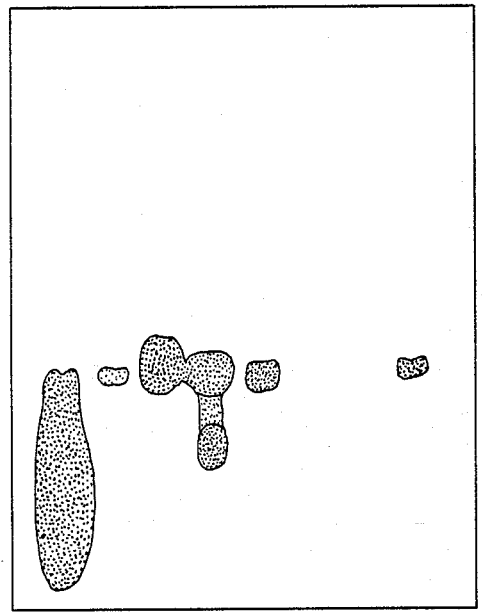
FIG. 1B
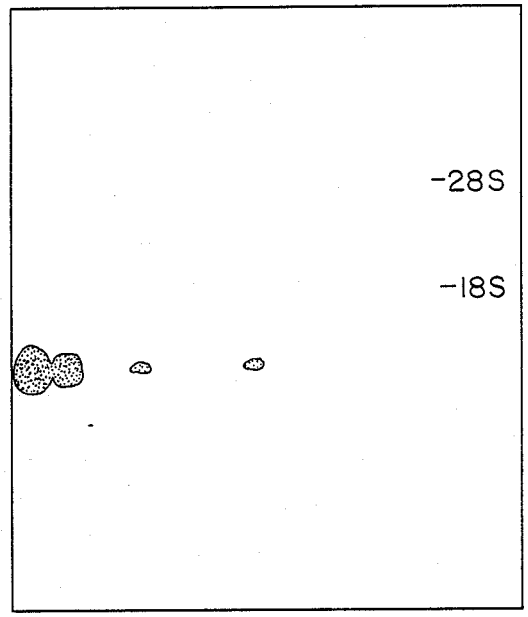
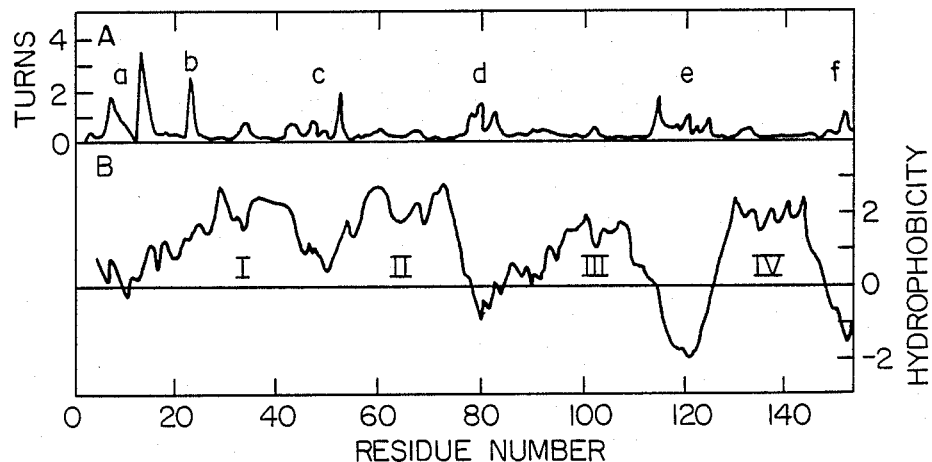
FIG. 3

FIG. 2-1

```
                                        CGGGAGTCTGAGCGGGCGCTCGTCCCGTCCCAAGGCCGACGCCAGCACGCCGTC
                                                        -40                     -20

1                                                                                                    30
  Met Ala Pro Ala Ala Thr Gly Gly Ser Thr Leu Pro Asp Thr Thr Leu Pro Ser Val Phe Ser Gly Phe Ile Phe Glu
  ATG GCC CCC GCA GCG GCG ACG GGG AGC ACC CTG CCC GAC ACC ACC TTG CCC AGT GGC TTC TTC ATC TTT GAG
  +1                    20                          40                        60
                                                                ↓
                                                                                                       60
  Phe Ile Phe Gly Gly Leu Val Trp Ile Leu Val Ala Ser Ser Leu Val Pro Trp Pro Leu Val Gln Gly Trp Val Met Phe Val Ser Val
  TTT ATC TTC GGG GGC CTG GTG TGG ATC CTG GTC GCC TCC TCC CTG GTC CCC TGG CCC CTG GTC CAG GGC TGG GTG ATG TTC GTG TCT GTG
                      100                         120                           140                         160                         180
                                ↓                                                                    ↓
                                                                                                       90
  Phe Cys Phe Val Ala Thr Thr Thr Leu Ile Ile Leu Tyr Ile Ile Gly Ala His Gly Glu Thr Ser Trp Val Thr Leu Asp Ala Ala
  TTC TGC TTC GTG GCC ACC ACC ACC TTG ATC ATC CTG TAC ATC ATA ATT GGA GCC CAC GGT GGA GAG ACT TCC TGG GTC ACC TTG GAC GCA GCC
                         200                        220                            240                        260
                                                                ↓
                                                                                                       120
  Tyr His Cys Thr Ala Ala Leu Phe Tyr Leu Leu Ser Ala Ser Val Leu Glu Ala Leu Ala Thr Ile Thr Met Gln Asp Gly Phe Thr Tyr Arg
  TAC CAC TGC ACC GCT GCC CTC TTT TAC CTC CTC AGC GCC TCA GTC CTG GAG GCC CTG GCC ACC ATC ACG ATG CAA GAC GGC TTC ACC TAC AGG
                      280                          300                          320                          340                        360
                         ↓                                                                    ↓
                                                                                                       150
  His Tyr His Glu Asn Ile Ala Ala Val Val Phe Ser Tyr Ile Ala Thr Leu Leu Tyr Val Val His Ala Val Phe Ser Leu Ile Arg Trp
  CAC TAC CAT GAA AAC ATT GCT GCC GTG GTG TTC TCC TAC ATA GCC ACT CTG CTC TAC GTG GTG CAT GCG GTG TTC TCT TTA ATC AGA TGG
                         380                          400                        420                        440
                                                                                    ↓
```

FIG. 2-2

```
Lys Ser Ser ***
AAG TCT TCA TAAAGCCGGCAGTAGAACTTGAGCTGAAAACCCAGATGGTGTTAACTGGCCGCCCCACTTTCCGGCATAACTTTTAGAAAACAGAAATGCCCTTGATGGTGGAAAAA
            460                   480                   500                   520                   540                   560

AGAAAACAACCACCCCCCACTGCCCAAAAAAAAGCCCTGCCCTGTGCTCGTGGGTGCTGTGTTACTCTCCGTGCCTTCGTGCCTTCGTGGGAGCTTGCTGTGTCTAACCTC
            580                   600                   620                   640                   660                   680

CAACTGCTGCTGTCTGCTAGGGTCACCTCCCTGTTTGTGAAAGGGGACCTTCTGTTCGGGGGTGGGAAGTGGCCACCGTGACCTGAGAAGGAAAGAAGATCCTCTGCTGACCCCTGG
            700                   720                   740                   760                   780                   800

AGCAGCTCTCGAGAACTACCTGTTGGTATTGTCCACACAAGCTCTCCCGAGGCGCCCATCTTGTGCCATGTTTAAGTCTTCATGGATGTTCTGCATGTCATGGGACTAAAACTCACCCAA
            820                   840                   860                   880                   900                   920

CAGATCTTTCCAGAGGTCCATGGTGGAAGACGATAACCCTGTGAAATACTTTATAAAATGTCTTAATGTTCAAAAAAAAAAAA
            940                   960                   980             1000  [POLY A]
```

T-CELL MEMBRANE PROTEIN

This invention was made with Government support under Grant numbers CA 42556 awarded by the National Institutes of Public Health. The Government has certain rights in the invention.

FIELD OF THE INVENTION

The present invention relates to a newly discovered human T-cell membrane protein which is produced in stage II and III T-cell development only, to immunogenic peptides derived from the protein, and to antibody and DNA probe compositions and methods for detecting, analyzing and/or sorting isolating T cells containing the protein.

REFERENCES

Alcover, A., Weiss, M.J., Daley, J.F., and Reinherz, E.L. (1986). Proc. Natl. Acad. Sci. USA 83, 2614–2618.

Aviv, H., and Leder, P. (1972). Proc. Natl. Acad. Sci. USA 69, 1408–1412.

Chirgwin, J.M., Przbyla, A.E., MacDonald, R.J., and Rutter, W.J. (1979). Biochemistry 18, 5294–5299.

Chou, P.Y., and Fasman, G.D. (1979). Ann. Rev. Biochem. 47, 251–276.

Claudio, T., Ballivet, M., Patrick, J., and Heinemann, S. (1983). Proc. Natl. Acad. Sci. USA 80, 1111–1115.

Collins, M.K.L., Tanigawa, G., Kissonerghis, A.-M., Ritter, M., Price, K.M., Tonegawa, S., and Owen, M.J. (1985). Proc. Natl. Acad. Sci. USA 82, 4503–4507.

Davis, M.M., Cohen, D.I., Nielsen, E.A., Steinmetz, M., Paul, N.E., and Hood, L. (1984). Proc. Natl. Acad. Sci. USA 81, 2149–2198.

De Coursey, T.E., Chandy, K.G., Gupta, S., Cahalan, M.D. (1984). Nature 307, 465–468.

Engelman, D.M., Goldman, A., and Steitz, T.A. (1982). 88, 82–88.

Finer-Moore, J., and Stroud, R.M. (1984). Proc. Natl. Acad. Sci. USA 81, 155–159.

Gold, D.P., Puck, J.M., Pettey, C.L., Cho. M., Coligan, J., Woody, J.N., and Terhorst, C. (1986). Nature 321, 431–434.

Greaves, M.F., Rao, J., Hariri, G., Verbi, N., Catovsky, D., Kung, P., and Goldstein, G. (1981). Leukemia Research 5, 281–299.

Haynes, B.F. (1986). In Leucocyte Typing II. Vol. 1, Human T Lymphocytes. Reinherz, E.L., Haynes, B.F., Nadler, L.M., and Bernstein, I.D., eds. (New York, Springer-Verlag), pp. 3–30.

Hedrick, S.M., Cohen, D.I., Nielsen, E.A., and Davis, M.M. (1984). Nature 308, 149–153.

Huynh, T., Young, R.A., and Davies, R.W. (1985). In DNA Cloning, A Practical Approach. D.M. Glover, ed. (Oxford, IRL Press).

Jackson, R.C., and Blobel, G. (1977). Proc, Natl. Acad. Sci. USA 74, 5598–5602.

Kopito, R.R., and Lodish, H.F. (1985). Nature 316, 234–238.

Kozak, M. (1984). Nucl. Acid Res. 12, 857–870.

Krebs, E.G., and Beavo, J.A. (1979). Ann. Rev. Biochem. 48, 923–959.

Kyte, J., and Doolittle, R.F. (1982). J. Mol. Biol. 157, 105–132.

Laemmli, U.K. (1970). Nature 227, 680–685.

Lee, J.S., Trowsdale, J., and Bodmer, W.F. (1980). J. Exp. Med. 152, 35–105.

McLauchlon, J., Gaffney, D., Whittan, J.L., and Clements, J.B. (1985). Nucl. Acid Res. 13, 1347–1369.

Maniatis, T., Fritch, E.F., and Sambrook, J. (1982). Molecular Cloning (Cold Spring Harbor, New York, Cold Spring Harbor Laboratory).

Melton, D.A., Krieg, P.A., Rebogliati, M.R., Maniatis, T., Zinn, K., and Green, M.R. (1984). Nucl. Acid Res. 12, 7035–7056.

Mueckler, M., Caruso, C., Baldwin, S.A., Panico, M., Blench, I., Morris, H.R., Allard, W.J., Lienhard, G.E., and Lodish, H.F. (1985). Science 229, 941–945.

Noda, M., Shimizu, S., Tanabe, T., Takai, T., Kayano, T., Ikeda T., Takahishi, H., Nakayama, H., Kanaoka, Y., Minamino, N., Kanagawa, K., Matsuo, H., Raftery, M.A., Hirose, T., Inayama, S., Hayashida, H., Miyata, T., and Numa, S. (1984). Nature 312, 121–127.

Oettgen, H.C., Terhorst, C., Cantley, L.C., and Rosoff, P.M. (1985). Cell 40, 583–590.

Proudfoot, N.J., and Brownlee, G.G. (1976). Nature 263, 211–214.

Reinherz, E.L., Kung, P.C., Goldstein, ??, Levey, R.H., and Schlossman, S.F. (1980). Proc. Natl. Acad. Sci. USA 77, 1588–1592.

Reinherz, E.L., Meuer, S.C., and Schlossman, S.F. (1983). Immunol. Today 4, 5–8.

Reinherz, E.L., and Schlossman, S.F. (1980). Cell 19, 821–827.

Royer, H.D., Ramarli, D., Acuto, O., Campen, T.J., and Reinherz, E.L. (1985). Proc. Natl. Acad. Sci. USA 82, 5510–5514.

Sanger, F., Nickler, S., and Coulson, A. (1977). Proc. Natl. Acad. Sci. USA 74, 5463–5467.

Sangster, R.N., Minowada, J., Suciu-Foca, N., Minden, M., and Mak, T.W. (1986). J. Exp. Med. 163, 1491–1508.

Schiffer, M., and Edmundson, A.B. (1967). Biophys. J. 7, 121–135.

Shapiro, D.N., Adams, B.S., and Niederhuber, J.H. (1985). J. Immunol. 134, 663–665.

Wallace, B.A. (1982). Methods in Enzymology 88, 447–462.

Weiss, A., Wiskocil, R.L., and Stobo, J.D. (1984). J. Immunol. 133, 123–128.

Wickner, W.T., and Lodish, H.F. (1985). Science 230, 400–407.

BACKGROUND OF THE INVENTION

T cells are a class of lymphocytes which mediate cellular immune responses in higher animals. When an organism is exposed to a foreign substance that can alter the surface of host cells, T cells that recognize the foreign antigen are activated, resulting in T-cell binding to and destruction of the altered cells.

The ontogeny of T cells, and the expression of different cellular antigens during T cell differentiation has been studied. T cells originate from precursor cells made in the bone marrow, and these cells further differentiate into virgin T cells in the thymus. A portion of the cells migrate from the thymus to T-cell domains of peripheral lymphoid organs. Probably as a result of antigen stimulation, some of the T cells are converted to long-lived mature T cells. The mature cells possess surface receptors for foreign antigens, and upon stimulation, proliferate to form functional T cells.

Monoclonal antibodies against T cells have been used to identify a number of surface molecules which are expressed during intrathymic ontogeny (Reinherz, 1983). This has allowed the definition of at least three discrete stages of T-cell differentiation (Reinherz, 1980). The earliest identified T-lineage cells express the sheep erythrocyte receptor, T11(stage I). Later, thymocytes express T6, T4 and T8 antigens (stage II). With further maturation, the expression of the surface antigen T6 is shut off, thymocytes acquire the T3/T-cell receptor structure and ultimately appear in the periphery as either T4+T8− or T4−T8+ cells (stage III).

Although monoclonal antibodies have helped define surface structures on T cells (Haynes), most T-cell surface molecules have remained elusive to serologic detection. There are as many as 200 different mRNA sequences expressed in T cells that are absent in B cells. A third of those sequences are membrane-associated molecules (Hedrick). Identification of membrane-associated molecules, and elucidation of their function and mechanism of action, is difficult because of the technical problems associated with the isolation and purification of proteins which have hydrophobic regions which can cause protein aggregation. In addition, there are limitations in the source of the product.

The problem of identifying surface antigens, and studying their role in cellular development and function, can also be approached with recombinant DNA methods. Potentially, these methods allow for the cloning and sequencing of coding sequences which are expressed specifically at certain developmental stages in T cells, and identification and expression of proteins and/or peptide regions associated with these coding sequences.

SUMMARY OF THE INVENTION

One object of the present invention is to provide antibody and DNA probe compositions and methods useful for distinguishing stage I T cells from more mature T cells.

Another object of the invention is to identify and produce by recombinant methods a T cell surface protein which is expressed in stages II and II/III, but not stage I, T cells only.

Still another object of the invention is to identify and produce immunogenic peptides derived from the novel protein, and to provide antibodies which are specific against the peptides.

Other objects of the invention are to provide methods which use the antibody for removing early or late-stage T cells selectively from a blood sample, and for monitoring certain types of leukemias.

The invention includes a 16.7 kilodalton human T-cell protein, designated herein as the MAL protein, which is produced in stages II and II/III, but not stage I, T cells. The protein has four distinct amphipathic domains, each having an amino acid composition which is predictive of an alpha helical structure that would be stable in a lipid bilayer. Each of these amphipathic domains is flanked by a relatively polar peptide domain whose amino acid composition is predictive of a $\beta$-pleat structure that would be stable in an aqueous environment.

A specific embodiment of the protein has the sequence:

```
1                                              10
Met Ala Pro Ala Ala Ala Thr Gly Gly Ser Thr Leu Pro Ser Gly 20                                30
Phe Ser Val Phe Thr Thr Leu Pro Asp Leu Leu Phe Ile Phe Glu

40
Phe Ile Phe Gly Gly Leu Val Trp Ile Leu Val Ala Ser Ser Leu 50                                60
Val Pro Trp Pro Leu Val Gln Gly Trp Val Met Phe Val Ser Val

70
Phe Cys Phe Val Ala Thr Thr Thr Leu Ile Ile Leu Tyr Ile Ile 80                                90
Gly Ala His Gly Gly Glu Thr Ser Trp Val Thr Leu Asp Ala Ala

100
Tyr His Cys Thr Ala Ala Leu Phe Tyr Leu Ser Ala Ser Val Leu 110                               120
Glu Ala Leu Ala Thr Ile Thr Met Gln Asp Gly Phe Thr Tyr Arg

130
His Tyr His Glu Asn Ile Ala Ala Val Val Phe Ser Tyr Ile Ala 140                               150
Thr Leu Leu Tyr Val Val His Ala Val Phe Ser Leu Ile Arg Trp

Lys Ser Ser
``` where the four amphipathic domains are defined by amino acids 15–41, 53–75, 95–113, and 126–148.

The flanking peptides in the above sequence are defined by amino acids 1–14, 42–52, 76–94, 114–125, and 149–153. One or more of these relatively polar peptides may be used as peptide antigens to produce antibodies specific against mature T cells. Preferred antigen are those defined by amino acid segments 76–94 and 114–125.

Another aspect of the invention is a DNA composition which codes for the full-length T-cell protein or for selected antigenic domains thereof. A preferred coding sequence derived from mature T cells has the sequence:

```
        • • •
CGCGGAGTCTGAGCGGCGCTCGTCCCGTCCCAAGGCCGACGCCAGCACGCCGTC
    −40                  −220                   −1

ATG GCC CCC GCA GCG GCG ACG GGG GGC AGC ACC CTG CCC AGT GGC
+1                   20                    40

TTC TCG GTC TTC ACC ACC TTG CCC GAC TTG CTC TTC ATC TTT GAG
               60                    80

TTT ATC TTC GGG GGC CTG GTG TGG ATC CTG GTG GCC TCC TCC CTG
          100                   120

GTG CCC TGG CCC CTG GTC CAG GGC TGG GTG ATC TTC GTG TCT GTG
    140                   160                   180

TTC TGC TTC GTG GCC ACC ACC ACC TTG ATC ATC CTG TAC ATA ATT
                      200                   220
```

-continued

```
GGA GCC CAC GGT GGA GAG ACT TCC TGG GTC ACC TTG GAC GCA GCC
            240                         260
TAC CAC TGC ACC GCT GCC CTC TTT TAC CTC AGC GCC TCA GTC CTG
        280                         300
GAG GCC CTG GCC ACC ATC ACG ATG CAA GAC GGC TTC ACC TAC AGG
    320                         340                         360
CAC TAC CAT GAA AAC ATT GCT GCC GTG GTG TTC TCC TAC ATA GCC
                    380                         400
ACT CTG CTC TAC GTG GTC CAT GCG GTG TTC TCT TTA ATC AGA TGG
            420                         440
AAG TCT TCA TAAAGCCGCAGTAGAACTTGAGCTGAAAACCCAGATGGTGTTAACTG
        460              480              500
GCCGCCCCACTTTCCGGCATAACTTTTTAGAAAACAGAAATGCCCTTGATGGTGGAAAAA
        520              540              560
AGAAAACAACCACCCCCCCACTGCCCAAAAAAAAAAAGCCCTGCCCTGTTGCTCGTGGGTG
        580              600              620
CTGTGTTTACTCTCCCGTGTGCCTTCGCGTCCGGGTTGGGAGCTTGCTGTGTCTAACCTC
        640              660              680
CAACTGCTGTGCTGTCTGCTAGGGTCACCTCCTGTTTGTGAAAGGGGACCTTCTTGTTCG
        700              720              740
GGGGTGGGAAGTGGCGACCGTGACCTGAGAAGGAAAGAAAGATCCTCTGCTGACCCCTGG
        760              780              800
AGCAGCTCTCGAGAACTACCTGTTGGTATTGTCCACAAGCTCTCCCGAGCGCCCCATCTT
        820              840              860
GTGCCATGTTTTAAGTCTTCATGGATGTTCTGCATGTCATGGGGACTAAAACTCACCCAA
        880              900              920
CAGATCTTTCCAGAGGTCCATGGTGGAAGACGATAACCCTGTGAAATACTTTATAAAATG
        940              960              980
TCTTAATGTTCAAAAAAAAAAAA
        1000    [POLY A]
```

The DNA composition may be used as a probe for detecting T cells which are active in MAL protein production, and in a recombinant peptide synthesis system for producing the MAL protein or peptides segments thereof, including antigenic peptides.

Antibodies prepared against the protein or immunogenic peptide regions thereof are useful for identifying mature T cells in a mixed cell sample, for purposes of cell sorting or assaying T cells in a selected developmental stage. The antibodies may also be used to distinguish different types or stages of leukemic T cells, on the basis of the presence or absence of the specific surface antigen.

These and objects and features of the present invention will becomes more fully apparent when the following detailed description of the invention is read in conjunction with the accompanying drawings.

BRIEF DESCRIPTION OF THE DRAWINGS

FIGS. 1A and 1B show RNA blot analyses of total RNA preparations from several cell types, when probed with a MAL protein coding sequence probe;

FIG. 2 shows the cDNA sequence and the corresponding amino acid sequence for the MAL protein;

FIG. 3 shows predicted turns (upper frame) and hydropathy (lower frame) plots for the amino acid sequence of the MAL protein;

DETAILED DESCRIPTION OF THE INVENTION

I. Definitions

Figure 4A:
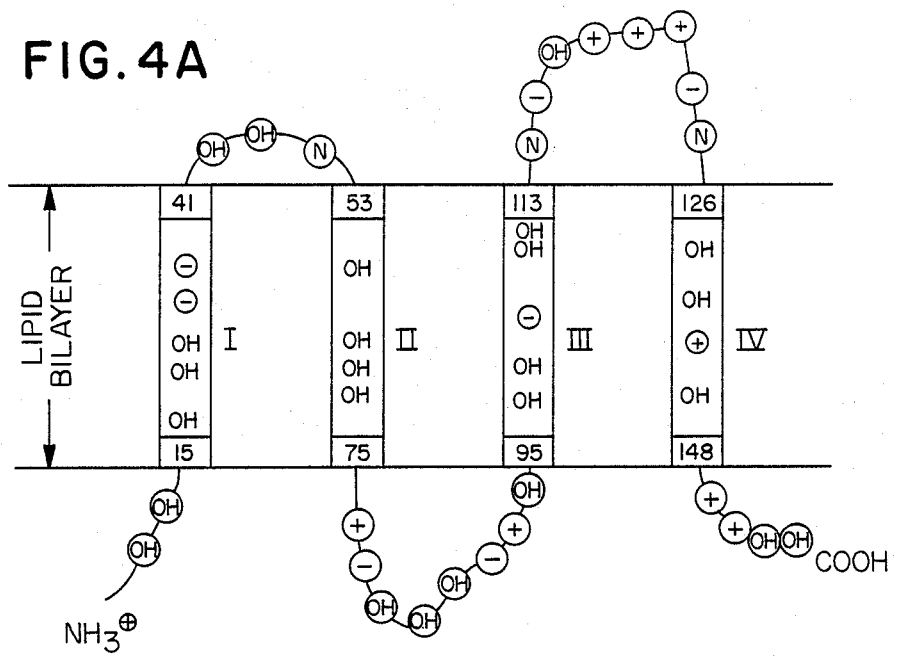
FIG. 4A presents a model for the membrane orientation of the MAL protein.

A "purified T-cell protein or peptide" refers to a composition in which the subject protein or peptide is substantially free of other T-cell components.

"MAL" refers to a T-cell protein with the following characteristics. It has a molecular weight of about 16.7 kilodaltons; four distinct and separate amphipathic domains, each having an amino acid composition which is predictive of an alpha helical structure that would be stable in a lipid bilayer; and is synthesized in stage II and stage II/III, but not stage I T cells. "MAL" also refers to mutants of this protein. These mutants may be detected by, for example, immunoassay techniques.

"Immunogenic peptides" of the MAL proteins refers to peptide segments of the MAL protein which, when injected into a laboratory animal, such as a mouse, rabbit, or goat, elicit antibodies which react specifically and with high affinity to the immunizing peptide.

A "coding sequence" is a polynucleotide sequence which may be transcribed and/or translated into a polypeptide when placed under the control of appropriate regulatory sequences.

II. Stage II T-Cell Coding Sequence

A coding sequence which is specific for mature T cells was identified using a strategy to isolate cDNA sequences to mRNAs which are expressed differentially during T-cell ontogeny. Leukemic cell lines are available which are representative of different stages of T-cell development (Reinherz, 1980; Greaves; Collins; Royer; and Sangster).

The strategy involved isolating cDNA sequences to mRNAs expressed in common in stage II and stage II/III of development. This was accomplished by synthesizing cDNAs to mRNAs present in MOLT-4 cells (Stage II), and in HPB-ALL cells (Stage II/III). Each of these cDNA preparations was depleted of sequences which annealed to mRNAs present in CCRF-HSB2 cells (Stage I). A library was constructed in pBR322 using the stage I depleted MOLT-4 cell cDNAs. To obtain cDNAs present in the MOLT-4 library which were also present during Stage II/III development, the library (about 3000 recombinants) was probed with Stage I depleted cDNAs derived from HPB-ALL cells. Five clones consistently hybridized with the probe. The largest cDNA insert, about 350 bp, was present in a clone designated pMA34. These cloning and selection methods are detailed in Example 1.

The clone pMA34 was used to determine whether mRNA corresponding to the cDNA insert was present specifically in T-cells in an advanced stage of differentiation. Total RNAs, isolated from a variety of cell lines and tissues, were analyzed by Northern blot analysis using nick translated pMA34 cDNA insert as a probe. Total RNA from the cells tested was denatured in the presence of 50% formamide and 2.2 M formaldehyde. 20 μg of each sample was subjected to electrophoresis on 1.2% agarose-formaldehyde gels. RNA transfer to Biodyne membranes, and hybridization with the probe were as described (Thomas). Final blot washing conditions were 0.1×SSC/0.1% sodium dodecyl sulfate (SDS) at 50° C.

In a first set of experiments, shown in FIG. 1A, radiolabeled pMA34 probe was used in blotting total RNA obtained from (a) membrane-associated RNA from Molt-4 cells (b) RNA from a T4+T8−helper T cell clone; (c) RNA from a T4−T8+helper T cell clone; (d) RNA from Molt-4 cells; (e) RNA from HPB-ALL cells; (f) RNA from human colon; (g) RNA from human adrenal glands; (h) RNA from human thymus; and (i) RNA from human liver. Lane b contains about half the total loaded RNA as the other lanes. The relatively large amount of material in lane a (membrane-associated RNA) indicates that the protein encoded by the RNA is a membrane-bound or secretory protein. The size of the probe-hybridizing bands in the figure is about 1.1 kb.

A second experiment aimed at identifying cells containing RNA which hybridizes to the pMA34 probe was similarly performed, with the results shown in FIG. 1B. Molt-4, HPB-ALL, and Jurkat are T-cell lines derived from patients with acute lymphoblastic leukemia. Their phenotype, as shown in Table 1, indicates that they are all Stage II or Stage II/III type cells. Other types of leukemic cells, i.e., CCRF-HSB2, CCRF-CEM, and another uncharacterized T-ALL leukemia cell line, T-ALL$_2$, did not contain RNA which hybridized to the probe. CCRF-HSB2 and CCRF-CEM are also T-cell lines derived from patients with acute lymphoblastic leukemia; however, they are characterized by a phenotype which is indicative of Stage I differentiation. The 1.1 kb hybridizing RNA band was also absent in the following cell lines: lines of B cell origin, i.e. JY, G7, and BL; an erythroleukemic cell line, K563; a promyelocytic cell line, HL 60; and HeLa cells. It was also absent in RNA extracted from the colon, adrenal glands and liver. However, the 1.1 kb hybridizing RNA band was present in RNA extracted from the thymus.

The above results indicate that an RNA which hybridizes with the pMA34 probe is expressed only in T-cells, and that the expression is unique to T-cells in mature stages (II and II/III) of differentiation. Hence, the protein produced by the coding sequence which is recognized by the probe can serve as a marker for these cells.

Full length cDNA recognized by the pMA34 probe was isolated from a Molt-4 cDNA library in λ-gt10, using the pMA34 insert as a probe, according to procedures outlined in Example 2. Nine positive clones were isolated from 50,000 recombinants; of these, six were analyzed for size of the cDNA. Five of the clones has cDNA corresponding to the 1.1 kb size of the mRNA detected by Northern blot analysis. The insert in one clone, λMA5, was sequenced as described in Example 2. The nucleotide sequence, and the corresponding amino acid sequence of the coded-for MAL protein, are shown in FIG. 2. As discussed in Example 2, the cDNA sequence does not result from a rearrangement of the genomic sequence, and the gene appears to be present as a single copy in the human genome, and contains at least one intron.

The coding sequence, and protions thereof, may be used to produce full length MAL protein or selected peptide regions thereof, according to standard recombinant DNA methods outlined below. In addition, the sequence or portions thereof are useful as probes for identifying mature T cells, as discussed in Section V below. The probes may be prepared by cloning and selection methods such as those discussed with reference to the pMA34 probe, or, for shorter probes, by conventional oligonucleotide synthesis methods.

III. The MAL Protein

FIG. 2 shows the amino acid sequence of the MAL protein determined from the coding sequence of the stage II-specific cDNA. The in-frame stop codons of the open reading frame are indicated by asterisks. Numbers shown above the amino acid sequence designate amino acid residue positions. Numbers beneath the nucleotide sequence show nucleotide positions. The nucleotides are numbered from the position of the presumed initiator methionine codon. The location of a putative polyadenylation signal (ATAAA) is underlined.

As shown in FIG. 2, a single open reading frame extends from the ATG at nucleotide 1 to the TAA stop codon at base 460; this encodes a protein with a predicted molecular weight of 16,700. The first Met codon has been assigned as the initiator because it is the first in-frame ATG downstream of the stop codon at base −45, and because the sequences flanking this ATG are homologous to the highly conserved sequence CCPurCC ATG G that flanks functional initiation sites in eukaryotic mRNAs (Kozak).

The nucleotide sequence between the translational stop codon for MAL and the 3'-terminus of the cDNA lacks a perfect consensus polyadenylation signal AA-TAAA, as described (Proudfoot). However, a number of cases exist in which this sequence is not present (Claudio, McLauchlon). The cDNA sequence for MAL does contain the sequence, ATAAAA, which is a putative polyadenylation signal. This putative signal is adjacent the sequence TGTCTTAA which is similar to the consensus sequence PyrGTGTTPyrPyr found between many polyadenylation signals and their poly(A) tails (McLauchlon).

The open reading frame shown in FIG. 2 encodes a protein of 153 amino acids. The amino acid sequence lacks N-glycosylation sites (Asn-X-Ser/Thr). There are two serines in the COOH-terminus of the molecule. The configuration of these serines resembles those favored by cAMP and cGMP dependent protein kinases (Krebs). The sequence indicates that MAL lacks an amino-terminal hydrophobic signal sequence. This signal sequence is characteristic of many membrane proteins (Wickner). However, transmembrane proteins which lack a cleavable signal peptide do exist, and the majority of these are thought to have their amino terminus on the cytoplasmic side of the membrane. Nevertheless, examples exist in which transmembrane proteins such as these have amino termini located in the extracytoplasmic space (Engelman).

The MAL nucleotide sequence and deduced amino acid sequences have no significant homology to any known DNA or protein sequences. This lack of significant homology was determined by a computer search through the GENBANK and Protein Identification Resource databases.

FIG. 3 shows a β-turns plot (upper frame) and a hydropathy (hydrophobicity) plot (lower frame) of the MAL protein, based on the MAL amino acid sequence. The β turns curve was generated by analysis of the sequence using a window of four amino acids, following the method of Chou and Fasman. Peak clusters corresponding to potential turns are named a, b, c, d, e, and f. The hydropathy plot was generated using the algorithm of Kyte and Doolittle. The curve is the average of the hydrophobicity index for each residue over a window of twenty residues. Positive values indicate hydrophobic regions and negative values, hydrophilic segments. The four hydrophobic regions which would appear to correspond to transmembrane domains are named I–IV.

The plots described in FIG. 3 predict that MAL has four hydrophobic regions of 19-25 amino acids, which correspond to peaks I-IV; these are interspersed with hydrophilic domains. The hydrophilic domains contain predicted β-turn secondary structure. Although a turn is predicted by peak b, which is due to Proline$_{23}$ in the first hydrophobic segment, the effect on the α-helix structure could be minimized because of the tendency of transmembrane segments to span the lipid bilayer as α-helices (Kyte). This pattern of hydrophobic domains of 19-25 amino acids alternating with hydrophilic segments has been reported for transmembrane proteins which have multiple spannings of the membrane (Wallace; Kopito, Mueckler).

A model for the membrane orientation of MAL is shown in FIG. 4A. In the figure, the four potential membrane-spanning domains are shown as rectangles. The relative positions of amino acid residues containing acidic (Glu, Asp), basic (Lys, Arg, His), hydroxyl (Ser, Thr) and amide (Gln, Asn) groups are indicated by (−), (+), (OH) and (N) signs, respectively. Histidine residues may be uncharged under physiological conditions. The model is not drawn to scale.

Figure 4B:
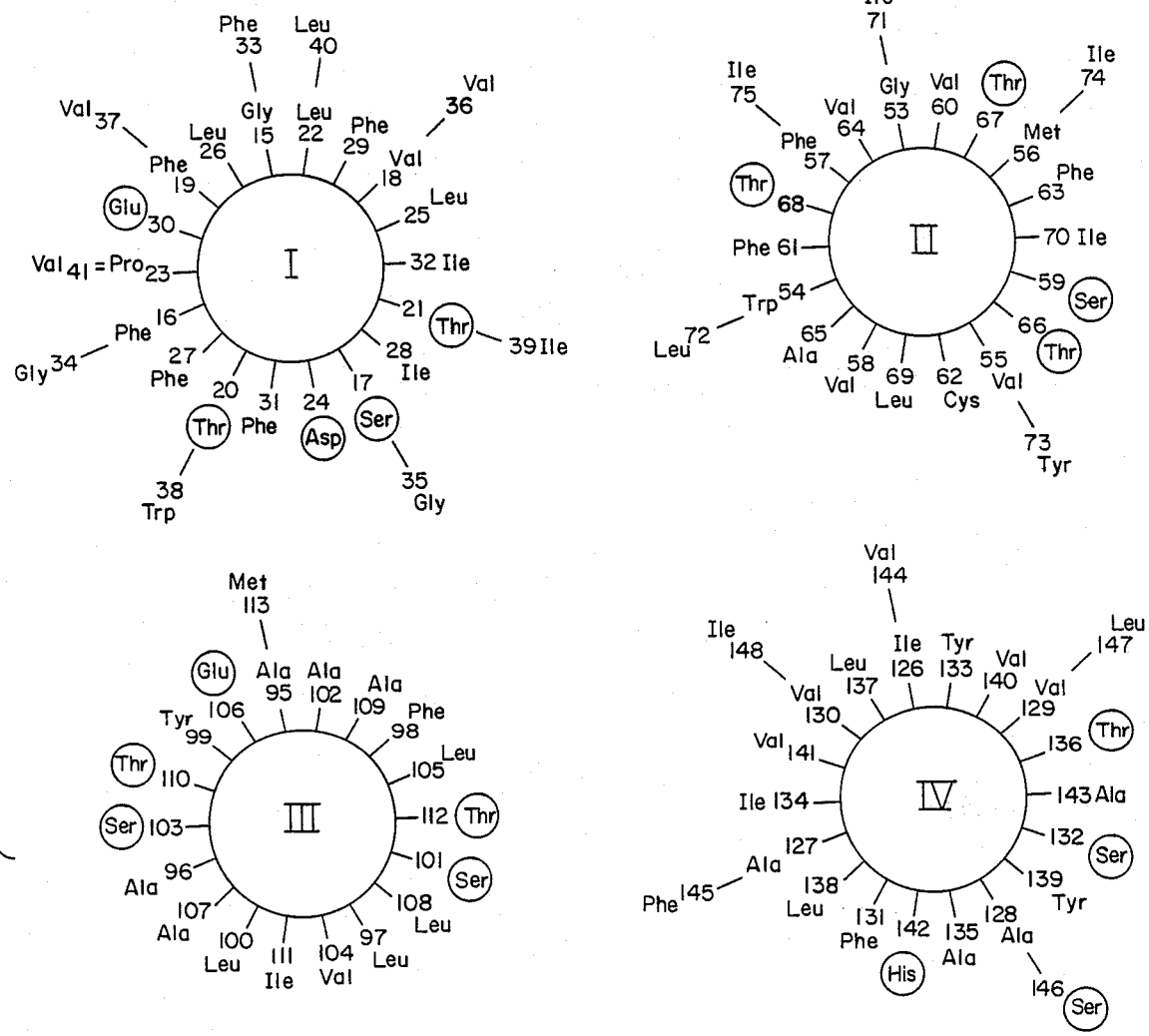
FIG. 4B shows an analysis of the α-helical regions of the MAL protein.

FIG. 4B shows an analysis of the α-helical regions of MAL, using the graphic method of Schiffer and Edmundson. The four potential transmembrane segments were plotted on two dimensional projections, called helical wheels. A periodicity of 3.6 residues per turn was assumed. Polar residues are circled, and charged amino acids are hatched. Analysis of the plot is suggestive that domain I is strongly amphipathic, since all of its polar groups face the same side of the α-helix. Domain IV is moderately amphipathic, and domains II and III contain some polar groups facing opposite sides of the helix. Transmembrane segments I and III contain charged residues. This pattern has previously been seen in a number of membrane transporters (Wallace, Kopito). The presence of amphipathic transmembrane domains in MAL suggests that it may line an aqueos channel.

The MAL protein can be obtained in purified form, according to one aspect of the invention, by transcription and expression of the recombinant MAL coding sequence. Example 3 describes the cloning of the full-length cDNA coding sequence into an RNA cloning vector, and translation of the RNA transcripts from the vector in a cell-free synthesizing system. Briefly, the cDNA insert was subcloned into the EcoRI site of the cDNA expression vector, pSP65, in the orientation indicated in FIG. 5A, using known procedures (Laemmli). The mRNAs transcribed from the linearized plasmid were used as templates in a cell-free protein synthesizing system, and the translation products were fractionated by SDS gel electrophoresis, with the results shown in FIG. 5b. The study reported in Example 3 indicates that the MAL protein migrates on the gel in aggregate form, and that in the absence of aggregation, the protein has the migration rate predicted from its 16.7 kd molecular weight.

A variety of expression systems are available for the synthesis of MAL or its fragments. These include prokaryotic expression systems, yeast systems, and higher eukaryotic systems which are known in the art. One preferred expression system is the λgt10 or λgt11 system (Huynh) which provides efficient expression of a β galactosidase fusion protein which (a) can be isolated by affinity chromatography with anti-β-gal antibody, and (b) can be subsequently cleaved from the β gal fusion moiety by conventional methods.

The invention also includes peptides, and particularly the following four hydrophilic peptides which flank the four transmembrane regions of the membrane:

| | |
|---|---|
| Met Ala Pro Ala Ala Ala Thr Gly Gly Ser Thr Leu Pro Ser | (a) |
| Ala Ser Ser Leu Val Pro Trp Pro Leu Val Gln | (b) |
| Gly Ala His Gly Gly Glu Thr Ser Trp Val Thr Leu Asp Ala Ala Tyr His Cys Thr | (c) |
| Gln Asp Gly Phe Thr Tyr Arg His Tyr His Glu Asn | (d) |

These peptide are prepared readily by standard solid-phase peptide synthesis methods, and are useful in preparing antibodies directed against the MAL protein, as will now be described.

III. Anti-MAL Antibodies

Antibodies which are specific against the MAL protein or peptides derived therefrom form another aspect of the invention. As indicated above, the antibodies are preferably formed against peptides which include one of the hydrophilic peptide regions flanking the four transmembrane regions of the MAL protein, since these peptides are readily prepared in purified form by synthetic methods, soluble in an aqueous medium, and more likely to be accessible to antibodies when the MAL protein is present in a membrane associated form. The four peptides are designated a–d above. Of these, the c and d peptides are preferred.

The antibodies may be prepared in polyclonal or monoclonal form. In both cases, a lab animal is initially immunized with the selected peptide (or the entire MAL protein), preferably derivatized to a carrier protein, such as keyhole limpet hemocyanin (KLH). The immunized animal is checked periodically during the immunization regimen for the presence of anti-peptide antibody in the serum. This assay can be carried out readily by a solid phase ELISA method, such as described in Example 4. In the case of polyclonal antibodies, a serum fraction obtained from the immunized animal may be subfractionated, if desired, to yield a partially purified immunoglobulin fraction containing the antibody of interest. Methods for generating polyclonal antibodies specific against the d peptide are described in Example 4.

Monoclonal antibodies are likewise prepared according to standard lymphocyte immortalization methods. Here $\beta$-lymphocytes from a successfully immunized animal, and preferably a mouse, are obtained from the blood or spleen, and immortalized by fusion with myeloma cells, preferably derived from the same species, e.g., mouse. The fusion products can be initially selected for production of antibody, then for production of antigen-specific antibodies by conventional cell-surface or solid-phase immunoassays, such as used in Example 4. Selected hybridomas which secrete the antibody of interest are maintained in culture, and the secreted antibody is harvested from the culture medium, by standard methods.

The polyclonal or monoclonal antibodies can be labeled by a suitable marker, such as a fluorescent or enzyme marker, for use in the T cell surface antigen assays described below.

V. Utility

A. DNA Probes

As seen above, probes, such as the pMA34 probe, derived from the MAL protein cDNA sequence, can be used to identify mature T cells specifically, based on hybridization with total cellular RNA. The assay may be used either to distinguish different stages of T-cell development, or different type of lymphocytic leukemias which are characterized by the presence of absence of the MAL protein, as discussed in Section II.

B. Antibodies

Antibodies specific against the MAL protein or its peptide fragments may likewise be used to assay for T-cell developmental stage, or for different types of leukemias, i.e., leukemias which arrest ontological development in a T-cell stage in which MAL is not expressed. In addition, remissions and/or cures of this type of leukemia may also be monitored using these antibodies to MAL, since MAL should be expressed in normal T lymphocytes which develop in the non-leukemic state. These diagnoses may be accomplished using the antibody in, for example, an enzyme-linked immunoassay system. Alternatively, flow cytometry methods give rapid and efficient identification of different cell types based on the binding of a marker antibody, such as a fluorescent-labeled antibody to the cell surfaces. Thus, the relative numbers of early (stage I) and mature (stages II and II/III) T cells in a blood sample can be determined readily by this method. Similarly, T cells obtained from a leukemia patient can be readily assayed by flow cytometry methods.

Mature T cells can also be selectively removed from a mixed cell population by complement mediated cell lysis in the presence of the antibody. Here the mixed cell population is reacted with the antibody in the presence of added serum complement, producing cell lysis which is specific to mature T cells.

Flow cytometry also allows the sorting of different-stage T cells in a blood-cell sample, in order to produce a blood sample enriched in one of the two cell types. This method would be practical, for example, to selectively remove mature T cells from a bone marrow cell preparation which is to be used for transplantation.

The antibody is also expected to be useful in studying the role of the MAL protein in T cell development and activation. Several lines of evidence suggest that the MAL protein is involved in ion transport across the T-cell membrane. Proteins involved in the transport of water-soluble molecules and ions across cellular membranes are believed to span the lipid bilayer several times (Hedrick; Wallace; Kopito). Such proteins often have hydrophilic residues confined to one face of the helix. Polar faces of adjacent helices, from the same or different subunits, could form a pore or a channel through the membrane (Wallace; Finer-Moore). In the case of ion channel proteins, at least one of the transmembrane domains is strongly amphipathic, and contains charged residues (Wallace; Finer-Moore). In addition, most of the sequenced membrane-transport proteins lack an $NH_2$—terminal signal peptide and some of them have both $NH_2$—and COOH-termini positioned in the cytoplasm (Kopito; Noda). Secondary structure predictions which support the hypothesis that MAL protein is involved in transport across the membrane are: (1) MAL has four potential transmembrane domains; (2) at least one of the presumed $\alpha$-helices spanning the membrane is strongly amphipatic and contains charged residues; (3) MAL lacks a $NH_2$ terminal signal peptide; and (4) the formation of oligomers in the in vitro translation reaction indicates that the MAL protein has a strong tendency to self-aggregate and suggests that the putative channel may be formed by a complex of MAL molecules. This does not rule out the possibility that in the cellular membrane MAL may be associated with different protein subunits.

No membrane proteins traversing the membrane multiple times have previously been described to be specifically associated with T-cells, although the existence of $K^+$(DeCoursey) and $Ca^{2+}$(Oettgen) channels in peripheral T-lymphocytes is well established. T-cell activation by mitogens (Weiss), antigens (Shapiro), or monoclonal antibodies against the T3/T-cell receptor protein complex (Imboden) or T11 glycoprotein (Alcover) results in an increase in cytoplasmic free $Ca^{2+}$. This has led a number of groups to postulate the existence of at least a $Ca^{2+}$ channel linked to the T11 structure and/or T3/T-cell receptor complex (Oettgen, Alcover). Based on the high labeling of the 20 kd nonglycosylated $\epsilon$ chain of the T3 complex with photoactivatable hydrophobic reagents, it was speculated that the $\epsilon$ subunit could be the putative $Ca^{2+}$ channel (Oettgen). However, molecular cloning of the cDNA encoding $\epsilon$ the chain of the T3 complex has shown that the deduced amino acids sequence for this protein predicts a structure with a unique membrane-spanning domain, similar to other single-spanning membrane proteins (Gold). The transmembrane arrangement of the MAL protein and its presence in leukemic T-cell lines expressing T11 and the T3/T-cell receptor protein complex (HPB-ALL and Jurkat) and in normal mature T-cell clones make MAL a candidate for involvement in membrane signaling in T-cells activated either via T11 or T-cell receptor pathways.

The secondary structure predictions for the deduced amino acid sequence of MAL postulate the existence of two highly charged segments (segments c and d). Antibodies against one or both of these would allow the function of the MAL protein, as it is affected by antibody binding, to be studied during cell activation and development.

Described below are examples of the present invention which are provided only for illustrative purposes, and not to limit the scope of the present invention. In light of the present disclosure, numerous embodiments within the scope of the claims will be apparent to those of ordinary skill in the art.

EXAMPLES

1. Materials and Methods

Enzymes were purchased from commercial sources, and used according to the manufacturers' directions. Radionucleotides and nitrocellulose filters were also purchased from commercial sources.

Plasmids were propagated in *E. coli* strain DHI. Lambda bacteriophage λgt10 was propagated in *E. coli* strain LE 392.

Cells were grown in RPMI-1640 supplemented with 10% fetal bovine serum at 37° C. in a 5% $CO_2$ atmosphere. Frozen human tissues were provided by the Department of Surgical Pathology of the Yale University School of Medicine.

Total cytoplasmic RNA from tissue culture cells was prepared by the Nonidet-P40 lysis method (Mueckler). Membrane-bound RNA was prepared by mechanical disruption of cells in hypotonic buffer and differential centrifugation (Lee). When frozen tissues were used, total RNA was isolated by homogenization in 4M guanidinium thiocyanate, followed by ultracentrifugation through a 5.7 M CsCl cushion (Chirgwin). Poly-(A)+RNA selection was achieved by oligo(dT)-cellulose chromatography (Aviv). High molecular weight genomic DNA was prepared conventionally (Maniatis).

The first strand of cDNAs were synthesized by oligo (dT) priming using poly(A)+RNA and RNA reverse transcriptase in the presence of 100 ng/ml actinomycin D.

In the cloning of DNA fragments, all DNA manipulations were done according to standard procedures. See Maniatis et al., supra. Restriction enzymes, T4 DNA ligase, *E. coli* DNA Polymerase I, Klenow fragment, and other biological reagents were purchased from commercial suppliers and used according to the manufacturers' directions. Double-stranded DNA fragments were separated on agarose gels and isolated by electroelution.

EXAMPLE 1

Stage II/III-Specific Library

This section descibes the preparation of a cDNA library from total stage II/III cDNA which has been depleted of stage I T-cell cDNA. This was accomplished by synthesizing cDNAs to mRNAs present in MOLT-4 cells (Stage II), and in HPB-ALL cells (Stage II/III). Each of these cDNA preparations was depleted of sequences which annealed to mRNAs present in CCRF-HSB2 cells (Stage I). A library was constructed in pBR322 using the stage I depleted MOLT-4 cell cDNAs. To obtain cDNAs present in the MOLT-4 library which were also present during Stage II/III development, the library was probed with Stage I depleted cDNAs derived from HPB-ALL cells.

More specifically, the first strand of cDNA was synthesized from poly (A)+RNA isolated from Molt-4 cells. The single stranded Molt-4 cDNA was mixed with a 10-fold mass excess of poly (A)+RNA from CCRF-HSB2 cells. The mixture was boiled for 60 sec and incubated at 68° C. in 0.5 M phosphate buffer/5 mM EDTA/0.1% SDS in a sealed glass capillary to a $R_o t$ value of 1,500 (Davis). Unhybridized cDNA was separated from the cDNA/RNA hybrids by chromatography on a hydroxyapatite column using 0.12M phosphate buffer/0.1% SDS at 60° C. The isolated single stranded cDNA fraction was used to construct a library in the EcoRI site of pBR322, using standard procedures, as described in Maniatis et al.

A cDNA probe was prepared from HPB-ALL cells as follows. The first strand of the cDNA was prepared from poly (A)+RNA isolated from HPB-ALL cells. The HPB-ALL cDNA was depleted of sequences which hybridized with an excess of poly (A)+RNA isolated from CCRF-HSB2 cells, using the conditions described above. These probes were labeled to specific activities of up to $10^9$ cpm/μg by conventional procedures (Davis).

About 3,000 recombinants were screened with the HPB-ALL cDNA probe. Screening of filters was carried out using $10^6$ cpm per 137 mm filter under standard conditions (Maniatis). Five clones hybridized consistently with the probe. One clone, pMA34, carried the largest insert, which was 350 bp.

EXAMPLE 2

Isolation of Full Length cDNA Which Encodes MAL

A full length cDNA encoding MAL was isolated from a Molt-4 (stage II) cDNA library prepared in λgt10, using the cDNA insert in pMA34 as a probe.

To prepare a Molt-4 cDNA library in λgt10, single stranded cDNAs were prepared as described above for construction of the Molt-4 cDNA library in pBR322. The second strand of cDNA was synthesized using RNase H, *E. coli* DNA polymerase, and T4 DNA ligase, as has been described (Gubler). cDNA molecules greater than 800 bp in length were cloned into the unique EcoRI site of λgt10, using published procedures (Huynh).

Recombinants in the unamplified library were screened with nick-translated pMA34 insert probe. Nine positive clones were isolated from the 50,000 recombinants screened. Six of the nine clones were analyzed for the size of the insert; five of the six clones analyzed had cDNA inserts the same 1.1 kb length as the mRNA detected by Northern blot analysis. One of these five clones, which contained a full length cDNA insert, was designated λMA5.

The complete sequence of the insert cDNA was obtained by sequencing both strands of the cDNA insert in λMA5. This was accomplished by subcloning the insert into ml3mp8, and sequencing by the dideoxy chain termination technique (Sanger).

To determine whether the cDNA sequence resulted from a rearrangement of genomic DNA sequences, genomic DNA from a variety of human cells expressing or not expressing MAL were hybridized with the isolated insert from λMA5. High molecular weight genomic DNA was isolated from a variety of human cells, only some of which express MAL mRNA. The DNAs were digested with either EcoRI or BamHI, electrophoresed on 0.8% agarose gels, and the DNA was transferred to Biodyne membranes. The filters were probed with the isolated insert of λMA5, which had been radiolabeled. Hybridization was as described by Southern. Filters were washed in 0.1×SSC (1×SSC=0.15 M NaCl/0.015M Na citrate, pH 7.0/0.1% SDS) at 65° C. The results showed no evidence of DNA rearrangements.

The full length MAL cDNA contains a single BamHI site and lacks an EcoRI site. Digestion of genomic DNA with the latter restriction enzyme yields two bands upon Southern blotting using the above described MAL cDNA probe. This suggests that the gene is present as a single copy in the human genome, and that it contains at least one intron.

EXAMPLE 3

Transcription and Translation of Full-Length MAL cDNA

Figure 5B:
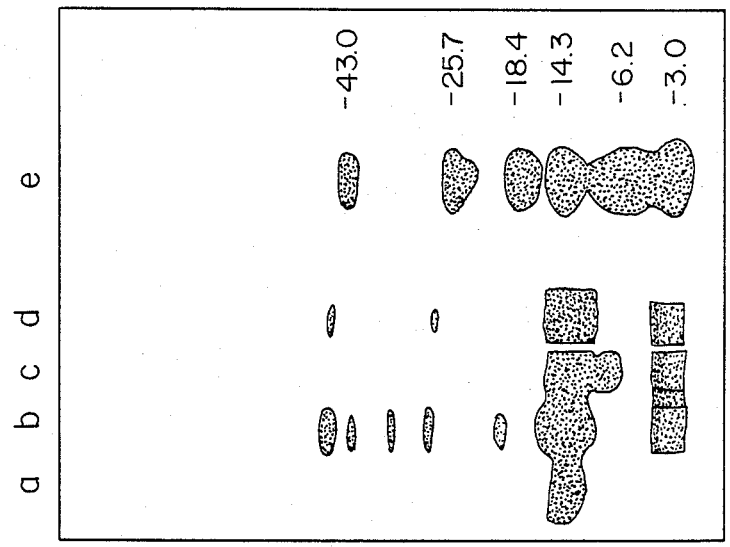
FIG. 5B shows an autoradiogram of the polypeptides synthesized in vitro using truncated or full length MAL mRNA, and separated on polyacrylamide gels.
Figure 5A:
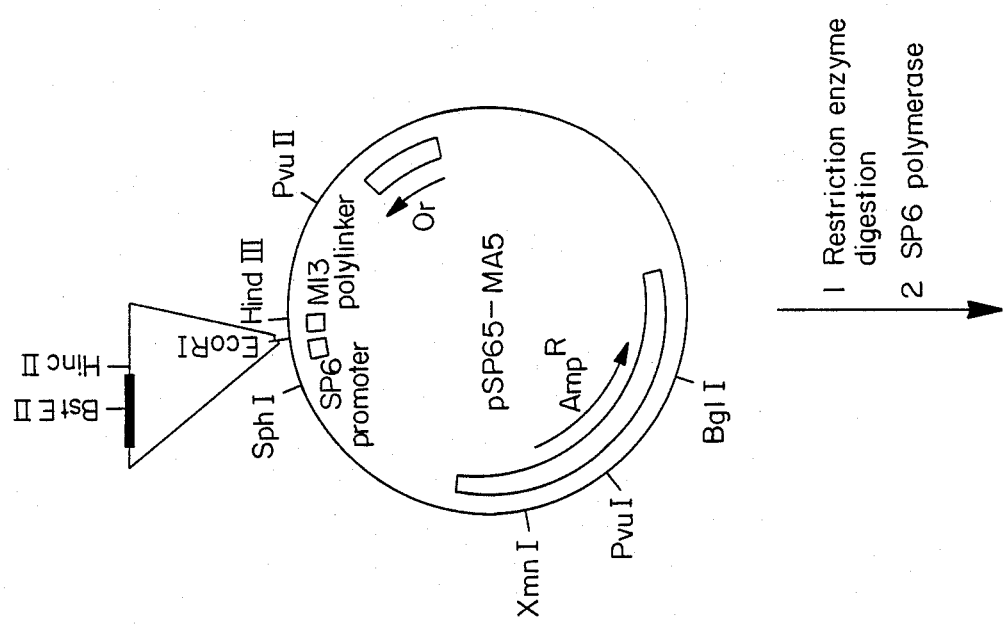
FIG. 5A shows the features of plasmid pSP65-MA5, and the relative sizes of the transcripts used for in vitro translation of MAL polypeptides.

The cDNA insert from λ-MA5 was subcloned into the EcoRI site of the cDNA expression vector, pSP65, in the orientation indicated in FIG. 4A, using published procedures (Laemmli). pSP65 contains the bacteriophage SP6 promoter (Melton). Plasmid DNA was linearized with BstEII, HincII, and Hind III. These enzymes cleave the plasmid DNA at the positions shown in FIG. 5A. Transcription of 2 μg linearized DNA by SP6 polymerase was in the presence of 0.5 mM$^{7m}$GpppG, and yielded synthetic $^{7m}$GpppG capped mRNAs. The mRNAs transcribed from the HindIII linearized plasmid were full length run-off transcripts. The mRNAs transcribed from BstEII and HincII-linearized plasmids were truncated run-off transcripts. The relative sizes of these mRNAs are illustrated in FIG. 5A.

The above described mRNAs were used as templates for in vitro translation using a commercially available rabbit reticulocyte system. Translation was in the presence of L-$^{35}$S methionine, under conditions suggested by the manufacturer. The in vitro translation products were subjected to electrophoresis on SDS-polyacrylamide gel under reducing conditions, using 7-15% acrylamide gels, as described by Laemmli. The translation products on the gel are shown in FIG. 5B.

Translation of the full-length RNA gave at least four discrete bands of apparent molecular mass of 20,000, 26,000, 32,000, and 40,000 (FIG. 5B), which were not present in the control without exogenous RNA (lane a vs. b). The position of these proteins and the presence of additional weak bands in the upper part of the gel suggest that they all represent oligomers either of the 20 kd protein or of a protein (∼14 kd) masked in the autoradiogram by the globin excess in the reticulocyte lysate. The same pattern was obtained when template RNA prepared from HincII-linearized plasmid was used (lane d). Since the HincII transcript does not contain enough information to encode proteins over 20 kd, this result rules out the possibility that the multiple bands were due to aberrant translation of the full-length RNA. When RNA synthesized from BstEII-linearized pSP65-MA5 was used as template for in vitro translation reactions, a single band of the predicted size was observed (lane c). This suggests that the COOH-terminal half of the molecule is responsible for both the aggregation and anomalous mobility of the MAL protein in SDS-polyacrylamide gels.

The presence of canine microsomal membranes (Jackson) in the in vitro translation mixture did not result in any alteration in the mobility of the proteins synthesized, ruling out the existence of a leader peptide sequence in the MAL protein.

EXAMPLE 4

Preparation of Anti-MAL Peptide Antibodies

A peptide having the sequence Gln Asp Gly Phe Thr Tyr Arg His Tyr His Glu Asn was prepared by conventional synthetic peptide methods. The peptide was linked to keyhole limpet hemocyanin (KLH) by glutaraldehyde crosslinking. The derivatized peptide was alum precipitated and this material was used to immunize rabbits by intradermal injection, according to standard procedures.

At various times during the immunization schedule, blood is collected from the immunized animals and tested for the presence of antibodies specific against the immunizing peptide, using conventional enzyme-linked immunoassay methods. Specifically, the peptide is attached covalently to a solid surface, and the solid surface reagent is reacted with test rabbit serum. After washing, the surface reagent is reacted with a commercially available enzyme-labeled anti-rabbit IgG, and assayed for the presence of the labeling enzyme. The desired antibody is obtained in partially purified form from the rabbit serum, and labeled with fluorescein isothiocyanate.

While the invention has been described with respect to particular methods and applications, it will be appreciated that various modifications and extensions in methodology and uses may be made without departing from the invention.

It is claimed:

1. A purified human T-cell protein which has the sequence:

1        10
Met Ala Pro Ala Ala Ala Thr Gly Gly Ser Thr Leu Pro Ser Gly 20        30
Phe Ser Val Phe Thr Thr Leu Pro Asp Leu Leu Phe Ile Phe Glu

40
Phe Ile Phe Gly Gly LeuVal Trp Ile Leu Val Ala Ser Ser Leu 50        60
Val Pro Trp Pro Leu Val Gln Gly Trp Val Met Phe Val Ser Val

70
Phe Cys Phe Val Ala Thr Thr Thr Leu Ile Ile Leu Tyr Ile Ile 80        90
Gly Ala His Gly Gly Glu Thr Ser Trp Val Thr Leu Asp Ala Ala

100
Tyr His Cys Thr Ala Ala Leu Phe Tyr Leu Ser Ala Ser Val Leu 110        120
Glu Ala Leu Ala Thr Ile Thr Met Gln Asp Gly Phe Thr Tyr Arg

130
His Tyr His Glu Asn Ile Ala Ala Val Val Phe Ser Tyr Ile Ala

-continued

```
                    140                        150
Thr Leu Leu Tyr Val Val His Ala Val Phe Ser Leu Ile Arg Trp

Lys Ser Ser.
```

2. A purified immunogenic peptide derived from a relatively polar region of a human T-cell protein, and having a sequence selected from the group consisting of:

Met Ala Pro Ala Ala Ala Thr Gly Gly Ser Thr Leu Pro Ser;  (a)
Ala Ser Ser Leu Val Pro Trp Pro Leu Val Gln;  (b)
Gly Ala His Gly Gly Glu Thr Ser Trp Val Thr Leu Asp Ala Ala Tyr His Cys Thr; and  (c)
Gln Asp Gly Phe Thr Tyr Arg His Tyr His Glu Asn.  (d)

3. The peptide of calim 2, selected from the group consisting of (c) and (d) only.

* * * * *